US011234831B2

(12) United States Patent
Sansur

(10) Patent No.: US 11,234,831 B2
(45) Date of Patent: Feb. 1, 2022

(54) CLOWARD-STYLE CERVICAL MESH CAGE WITH LATERAL STABILIZERS

(71) Applicant: UNIVERSITY OF MARYLAND, BALTIMORE, Baltimore, MD (US)

(72) Inventor: Charles Sansur, Towson, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 43 days.

(21) Appl. No.: 16/607,440

(22) PCT Filed: Apr. 24, 2018

(86) PCT No.: PCT/US2018/029064
§ 371 (c)(1),
(2) Date: Oct. 23, 2019

(87) PCT Pub. No.: WO2018/200469
PCT Pub. Date: Nov. 1, 2018

(65) Prior Publication Data
US 2020/0129305 A1    Apr. 30, 2020

Related U.S. Application Data

(60) Provisional application No. 62/489,080, filed on Apr. 24, 2017.

(51) Int. Cl.
*A61F 2/44* (2006.01)
*A61F 2/30* (2006.01)
*A61F 2/28* (2006.01)

(52) U.S. Cl.
CPC .......... *A61F 2/446* (2013.01); *A61F 2/30749* (2013.01); *A61F 2/3094* (2013.01);
(Continued)

(58) Field of Classification Search
CPC .......... A61F 2/445; A61F 2/446; A61F 2/447; A61F 2/30749
See application file for complete search history.

(56) References Cited

U.S. PATENT DOCUMENTS

| 5,683,394 A | 11/1997 | Rinner |
| 5,709,683 A | 1/1998 | Bagby |

(Continued)

FOREIGN PATENT DOCUMENTS

| CN | 105853032 | 8/2016 |
| WO | 1997/23174 | 7/1997 |

OTHER PUBLICATIONS

International Preliminary Report on Patentability dated Oct. 29, 2019 in International (PCT) Application No. PCT/US18/029064.
(Continued)

*Primary Examiner* — Brian A Dukert
(74) *Attorney, Agent, or Firm* — Wenderoth, Lind & Ponack, L.L.P.

(57) ABSTRACT

A Cloward-style cage device for anterior cervical fusion and fixation includes a body and a lateral stabilizer. The device uses the historical Cloward-style approach, and, as such, decompresses the interbody disc. The device can be used with a cylindrical drill bit to drill through the interbody disc to remove a portion of the interbody endplates to decompress a remaining portion of the interbody disc. The lateral portions of the endplates are generally preserved. The device has a cylindrical body formed of a mesh-like material, with lateral stabilizers.

10 Claims, 9 Drawing Sheets

(52) U.S. Cl.
CPC ....... *A61F 2/447* (2013.01); *A61F 2002/2835* (2013.01); *A61F 2002/30164* (2013.01); *A61F 2002/30476* (2013.01); *A61F 2002/30578* (2013.01); *A61F 2002/4495* (2013.01); *A61F 2310/00017* (2013.01); *A61F 2310/00023* (2013.01)

(56) References Cited

U.S. PATENT DOCUMENTS

| | | |
|---|---|---|
| 6,332,895 B1 | 12/2001 | Suddaby |
| 6,371,986 B1 | 4/2002 | Bagby |
| 6,371,987 B1 | 4/2002 | Weiland et al. |
| 6,547,823 B2 | 4/2003 | Scarborough et al. |
| 6,582,431 B1 | 6/2003 | Ray |
| 6,981,975 B2 | 1/2006 | Michelson |
| 8,617,244 B2 | 12/2013 | Reichen et al. |
| 8,932,358 B1 | 1/2015 | Nehls |
| 9,427,328 B2 | 8/2016 | Drochner et al. |
| 2001/0020185 A1 | 9/2001 | Ray |
| 2001/0034553 A1 | 10/2001 | Michelson |
| 2002/0138146 A1* | 9/2002 | Jackson ................ A61F 2/4455 623/17.15 |
| 2003/0149484 A1 | 8/2003 | Michelson |
| 2003/0204261 A1 | 10/2003 | Eisermann et al. |
| 2006/0167547 A1 | 7/2006 | Suddaby |
| 2008/0188941 A1 | 8/2008 | Grotz |
| 2010/0286785 A1 | 11/2010 | Grayson |
| 2012/0065688 A1 | 3/2012 | Nehls |

OTHER PUBLICATIONS

Extended European Search Report dated Jan. 12, 2021, in corresponding European Patent Application No. 18791664.8.
International Search Report dated Jul. 20, 2018 in International Application No. PCT/US18/29064.
Written Opinion of the International Searching Authority dated Jul. 20, 2018 in International Application No. PCT/US18/29064.

* cited by examiner

CLOWARD-STYLE CERVICAL MESH CAGE WITH LATERAL STABILIZERS

TECHNICAL FIELD

The present application relates to Cloward-style cage devices for anterior cervical fusion and fixation that include a body and lateral stabilizers. The devices can be used with a cylindrical drill bit to drill through the interbody disc to remove a portion of the interbody endplates to decompress a remaining portion of the interbody disc and the spinal canal and neural foramen. The lateral portions of the endplates are generally preserved. The device has a cylindrical body formed of a mesh-like material with lateral stabilizers involving the lateral aspect of endplates and uncovertebral joints. In one embodiment, the cage device also includes integrated fixation holes to allow fixation to the vertebral bodies using either screws, pins, or bone anchors. These screws, pins, or anchors would then be secured to the device through locking pins or screws. In an additional embodiment, the cage contains an anterior metal extension that protrudes cephalad and caudal to prevent impaction of cage into spinal canal. One embodiment also uses teeth on the surface of lateral wings to prevent anterior migration of device.

BACKGROUND

The current Cloward technique is an anterior cervical discectomy and fusion ("ACDF") technique that uses a solid cylindrical allograft or auto-graft bone dowel-type graft inserted into a cervical interbody space to increase the interbody height to decompress the spinal cord and nerve roots. The ACDF technique is used to treat spinal cervical abnormalities, such as spondylosis, herniated discs, fractures, and neoplastic lesions. Generally, the technique uses a large drill to remove a volume for bone graft by removing not only the discs, but also the central portion of vertebral endplates to give a better opportunity to decompress neural structures anteriorly.

However, the current Cloward techniques do not use the remaining portion of the cervical endplate after drilling. Thus, subsidence, which is a decrease of anterior or posterior disc height, is more likely and can cause kyphosis, affect adjacent segment disease, and lower the rate of fusion. Alternative anterior cervical procedures use a standard Smith-Peterson approach, which often leaves residual osteophytes if the endplates are not completely removed. However, subsidence is likely to occur when endplates are completely removed. Furthermore, when endplates are preserved to reduce the risk of subsidence, there is increased risk of pseudoarthrosis.

BRIEF SUMMARY

The devices and techniques of the present application give the opportunity to decompress the interbody cervical space by using a modified Cloward-style device. The device substantially reduces the risk of subsidence compared to typical Cloward-style and other devices. The device allows for a bone plug or cage insertion and grafting, which reduces the likelihood that the bone plug will loosen. The Cloward-style device according to one or more embodiments allows the physician to remove substantially all of the desired osteophyte material, and allows the physician to preserve the partial endplates of the body. The devices further use the preserved lateral endplates and uncovertebral joint to support and distract the interbody height. Simultaneously, a cylindrical hole-like defect in the center allows one to remove large osteophytes. At least one embodiment of the device is configured to stabilize the device translationally and rotationally within the defect. Another embodiment of the device is configured to allow the physician to secure a lordotic angle, which generally relates to optimizing the curvature of a patient's cervical spine. Another embodiment of device is configured to comprise a cylindrical mesh like cage that contains internal lateral interbody wings, where the wings are then deployed laterally through an expansion mechanism that is controlled from the center of the cylinder.

A typical Cloward-style technique allows for decompression, even in the setting of large osteophytes, but generally provides unsatisfactory fixation strength. However, the Cloward-style devices of the present application take advantage of the decompression capabilities of the established Cloward-style technique and provides a more modern instrumentation solution to enhance fixation properties, with the opportunity to utilize the remaining lateral endplates to improve surface area for bone fusion, and reduce subsidence. Thus, the Cloward-style devices of the present application provide an effective solution to at least the above-mentioned problems with known devices and techniques. Furthermore, by removing the central portion of endplates at the involved vertebral segment, exposure of the interbody space to the bone marrow of the vertebral bodies can enhance osseous union and help reduce the incidence of pseudoarthrosis.

In a first embodiment, the cervical mesh cage device comprises a cylindrical body having a proximal end and a distal end, an endplate fixed to the cylindrical body at the proximal end, wherein the endplate comprises fastener apertures, and a lateral stabilizer. The lateral stabilizer can be a removable wing that removably attaches to the cylindrical body. Further, the lateral stabilizer can be configured to slidably attach to the cylindrical body by sliding axially along a groove on an outer surface of the cylindrical body. The cervical mesh cage device can also include one or more locking mechanisms that secures the lateral stabilizer to the cylindrical body. Also, the cervical mesh cage device can include fasteners that are configured to fix the cervical mesh cage device to a first cervical vertebra and a second cervical vertebra via the fastener apertures. The plurality of fastener apertures of the cervical mesh cage device can be angled divergently from an axis running through the cylindrical body. Further, the cylindrical body can be configured to promote bone growth by providing at least one of a plurality of apertures in the cylindrical body or an outer surface treatment to the cylindrical body.

A method of inserting the cervical mesh cage device according to the first embodiment comprises drilling a defect in a spine to remove a portion of bone; inserting the cervical mesh cage device into the defect; and fastening the cervical mesh cage device to a first cervical vertebra and a second cervical vertebra in the spine. The method can further comprise placing a bone graft material into the cylindrical body.

In a second embodiment, the cervical mesh cage device comprises a cylindrical body comprising a top portion and a bottom portion, wherein the cylindrical body has a proximal end and a distal end, an endplate comprising a top endplate and a bottom endplate, wherein the top endplate is fixed to the top portion of the cylindrical body at the proximal end, wherein the bottom endplate is fixed to the bottom portion of the cylindrical body at the proximal end, and wherein the endplate comprises fastener apertures, and lateral stabilizers, wherein the top portion of the cylindrical body and the bottom portion of the cylindrical body are joined by a joint at the distal end of the cylindrical body. The cervical mesh cage device according to the second embodiment, can further comprise a wedge insert. In the cervical mesh cage device according to the second embodiment, the top portion of the cylindrical body and the bottom portion of the cylindrical body can have joint faces that are configured to mate the top portion of the cylindrical body with the bottom portion of the cylindrical body. Also, the wedge insert can be a pair of strut spacers, and the top portion of the cylindrical body and the bottom portion of the cylindrical body can have joint faces that are configured to mate the top portion of the cylindrical body with a top portion of the strut spacers and the bottom portion of the cylindrical body with a bottom portion of the strut spacers. The cervical mesh cage device according to the second embodiment can further comprise a plurality of fasteners configured to fix the cervical mesh cage device to both a first cervical vertebra and a second cervical vertebra via the fastener apertures. The top portion of the cylindrical body and the bottom portion of the cylindrical body can be joined by the joint to form an angle of between 0 degrees and approximately 25 degrees. The lateral stabilizers can extend from the top portion of the cylindrical body and the bottom portion of the cylindrical body in a direction that is radially outward with respect to a central axis of the cylindrical body. The lateral stabilizers can further extend into the cylindrical body. In cervical mesh cage device according to the second embodiment, the strut spacers can be configured to fix an angle between the top portion of the cylindrical body and the bottom portion of the cylindrical body.

A method of inserting the cervical mesh cage device according to the second embodiment comprises drilling a defect in a spine to remove a portion of bone; inserting the cervical mesh cage device into the defect; and fastening the cervical mesh cage device to a first cervical vertebra and a second cervical vertebra in the spine. The method can further comprise placing a bone graft material into the cylindrical body.

In a third embodiment, the cervical mesh cage device comprises a cylindrical body comprising a top portion having a top joint face and a bottom portion having a bottom joint face, wherein the top joint face and the bottom joint face extend in a direction that is radially outward with respect to a central axis of the cylindrical body to form lateral stabilizers, and wherein the top portion of the cylindrical body and the bottom portion of the cylindrical body comprise one or more fixation holes that allow fasteners to be secured from within the cervical mesh cage device. The cervical mesh cage device can further comprise a wedge insert that is a pair of strut spacers, wherein the top portion of the cylindrical body and the bottom portion of the cylindrical body can be configured to mate the top joint face with a top portion of the strut spacers and the bottom joint face with a bottom portion of the strut spacers.

A method of inserting the cervical mesh cage device according to the third embodiment comprises drilling a defect in a spine to remove a portion of bone; inserting the cervical mesh cage device into the defect; and fastening the cervical mesh cage device to a first cervical vertebra and a second cervical vertebra in the spine.

In a fourth embodiment, the cervical mesh cage device comprises a cylindrical body having a proximal end and a distal end, an endplate fixed to the cylindrical body at the proximal end, wherein the endplate comprises fastener apertures, and an expandable lateral stabilization mechanism, wherein the expandable lateral stabilization mechanism comprises a cage expansion mechanism and a lateral stabilizer, wherein the cage expansion mechanism is configured to cause the expandable lateral stabilization mechanism to expand in a radial direction from the cylindrical body.

A method of inserting the cervical mesh cage device according to the fourth embodiment comprises drilling a defect in a spine to remove a portion of bone; inserting the cervical mesh cage device into the defect; expanding the expandable lateral stabilization mechanism; and fastening the cervical mesh cage device to a first cervical vertebra and a second cervical vertebra in the spine. The method can further comprise placing a bone graft material into the cylindrical body.

Each of the embodiments disclosed herein can be used to treat spinal cervical abnormalities. Thus, the embodiments include the use of the embodiments to treat spinal cervical abnormalities, including, but not limited to, spondylosis, herniated discs, fractures, and neoplastic.

BRIEF DESCRIPTION OF THE DRAWINGS

The advantages and features of the one or more embodiments of the present application will become more readily apparent by reference to the exemplary, and therefore non-limiting, embodiments illustrated in the drawings.

DETAILED DESCRIPTION

First Embodiment

Figure 1:
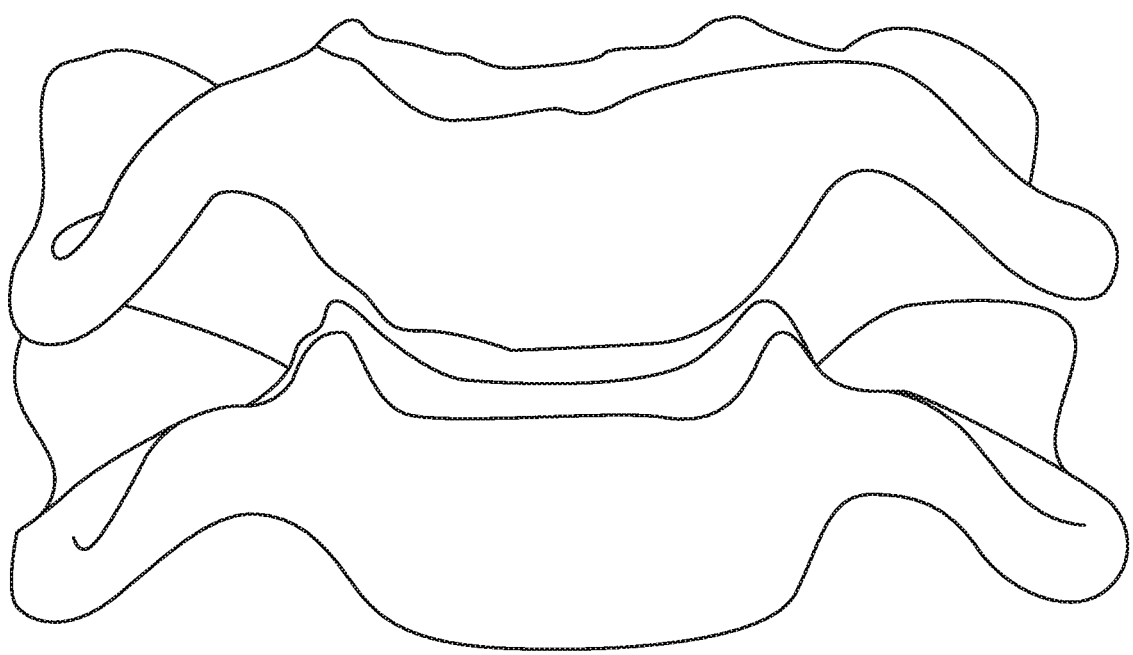
FIG. 1 is an illustration of a standard anterior cervical approach.
Figure 2:
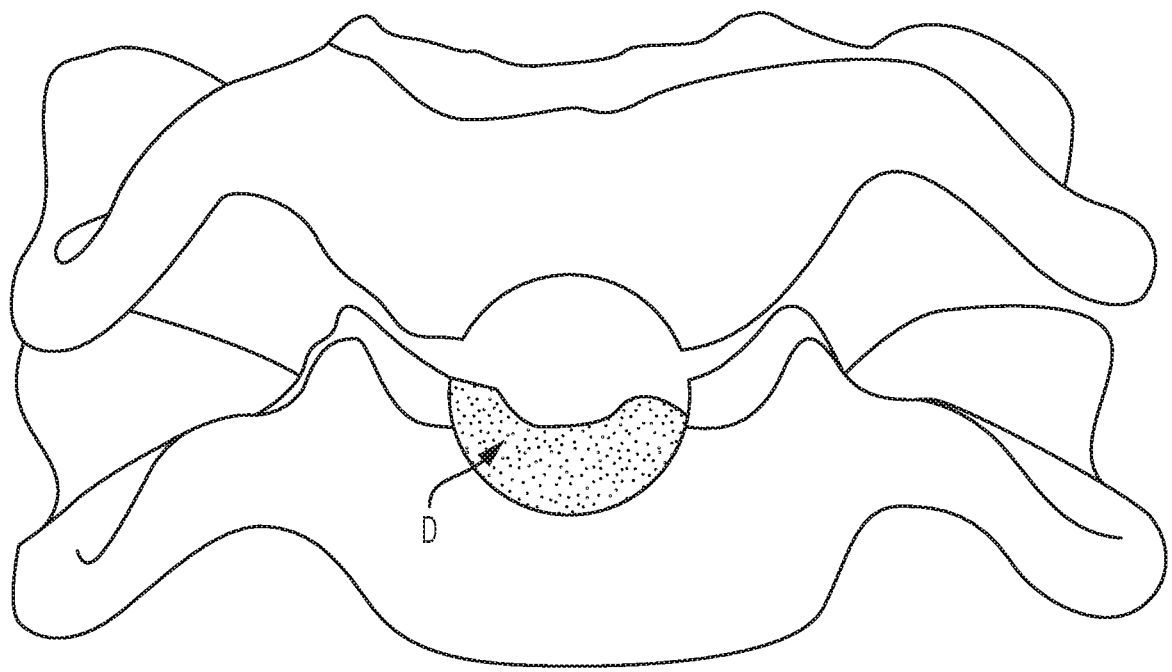
FIG. 2 is an illustration of interbody discs having a drilled defect.
Figure 3:
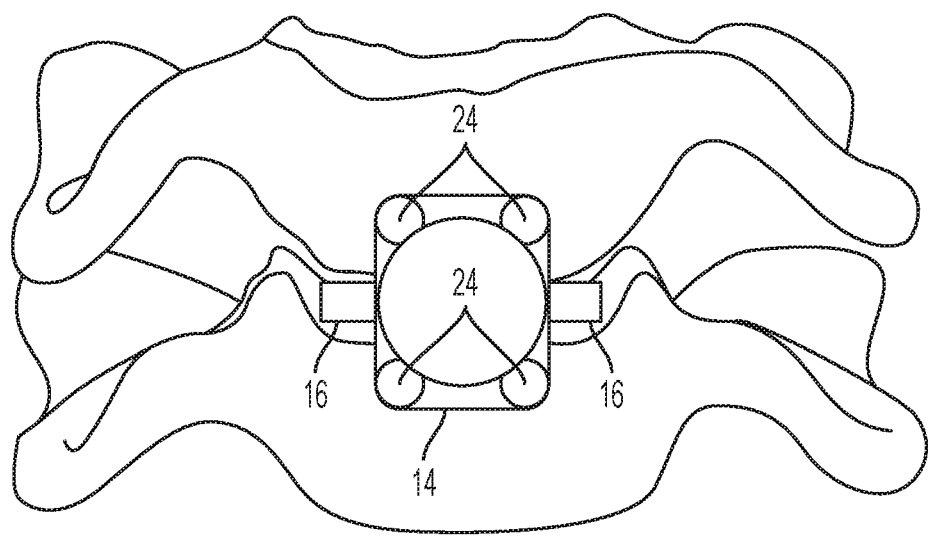
FIG. 3 is an illustration of an embodiment of a Cloward-style cervical mesh cage device inserted in the drilled defect of FIG. 2.

Referring to FIGS. 2-8, an embodiment of a Cloward-style cervical mesh cage device 10 or plate cage is configured to reduce compression of a patient's interbody cervical bones, also known as the interbody discs or endplates. FIG. 2 shows interbody cervical bones, wherein a cylindrical drill bit has removed bone to allow for a satisfactory decompression of midline compression and foraminal disease. The current embodiment of the device 10 is further configured to fit within a defect D formed in the patient's interbody cervical bones, as further described below and shown in FIG. 2. The device 10 includes a cylindrical body 12, an endplate 14, and a lateral stabilizer, and can include fasteners 18. As seen in FIG. 3, for example, the lateral stabilizer can be a pair of lateral stabilizers 16, where each member of the pair of lateral stabilizers 16 can be located on substantially opposite sides of the body 12. The body 12 is a generally hollow cylindrical body 12 having a proximal end 20 and a distal end 22, wherein the endplate 14 is fixed to the cylindrical body 12 at the proximal end 20. The cylindrical body 12 is configured to frictionally fit within a diameter of the defect D. In the current embodiment, the cylindrical body 12 has an outer surface with a diameter that is slightly smaller than the diameter of the defect D.

A physician can advantageously press the cylindrical body 12 within the defect D (see FIGS. 2 and 3) with only manual force, such as hand force. However, some instances may occur in which friction between the outer surface of the cylindrical body and inner surface of the defect D is sufficiently high, such that the physician may require a tool, such as a mallet, to create sufficient force to insert the cylindrical body 12 into the defect D. For example, friction between the outer surface of the cylindrical body 12 and inner surface of the defect D may be high because at least one of the outer surface of the cylindrical body 12 and the inner surface of the defect D has a surface treatment, as further described below, or the diameter of the defect D is smaller than the diameter of the cylindrical body 12.

As stated above, the cylindrical body 12 is configured to frictionally fit within the defect D such that the device 10 may fit stably within the defect D over a long period of time. For example, the cylindrical body 12 generally fits within the defect D without requiring a physician to readjust the position or orientation of the device 10 caused by substantial loosening of the cylindrical body 12 within the defect D.

In one embodiment, the cylindrical body 12 is configured to promote bone growth of the cervical bones into the outer surface of the device 10 to further fixate the device 10 within the interbody defect D. In the current embodiment, the outer surface is configured to promote bone growth, such as by having an outer surface treatment, including a roughened surface, a porous surface, or the like, to generally increase fixation properties and/or surface area of the outer surface. Furthermore, in one embodiment the outer surface treatment may be a coating to promote such bone growth. In another embodiment, the cylindrical body 12 has plurality of apertures from the outer surface to the inner surface, such that the patient's bone can grow through the apertures to a bone graft material B that is within the cylindrical body 12. In yet another embodiment, the cylindrical body 12 includes the plurality of apertures, such as those of a mesh, and the outer surface treatment to promote bone growth.

The endplate 14 is configured to be adjacent to an anterior face of the cervical bones when the cylindrical body 12 is in the defect D, and to allow the bone graft material B to be placed within the cylindrical body 12 when the device 10 is in the defect D. The endplate 14 of the current embodiment has a generally rectangular-like outer shape with a central aperture and the set of fastener apertures 24. The central aperture has a diameter that is approximately equal to the inner diameter of the cylindrical body 12, such that a bone graft material B can be placed within the cylindrical body 12 when the device 10 is in the defect D. The patient's bone is then able to better fixate to the bone graft material B and device 10 to secure the device 10.

Figure 4:
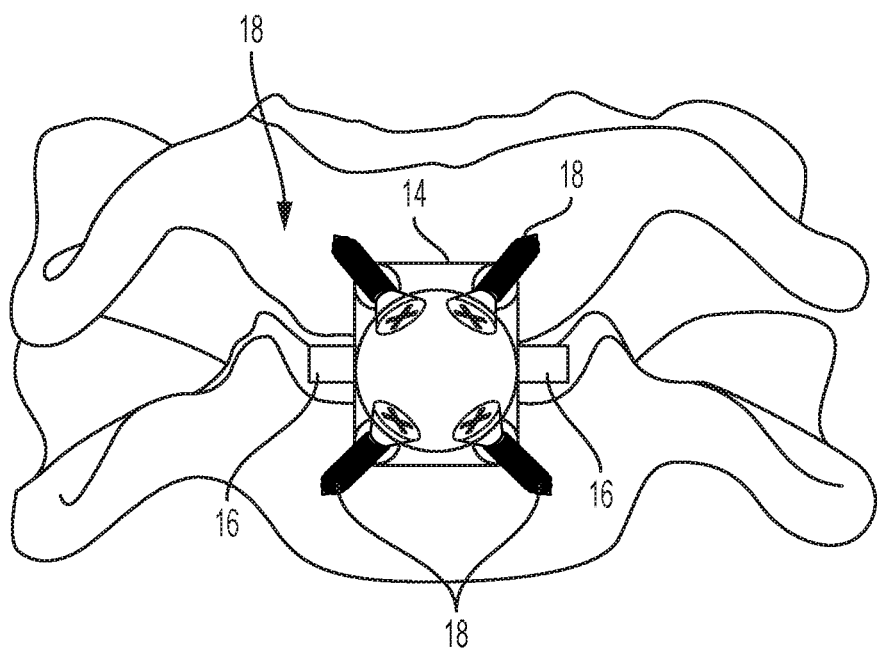
FIG. 4 is an illustration of the embodiment of the Cloward-style cervical mesh cage device of FIG. 3 inserted in the defect and having fasteners fastened to vertebral bodies.
Figure 5:
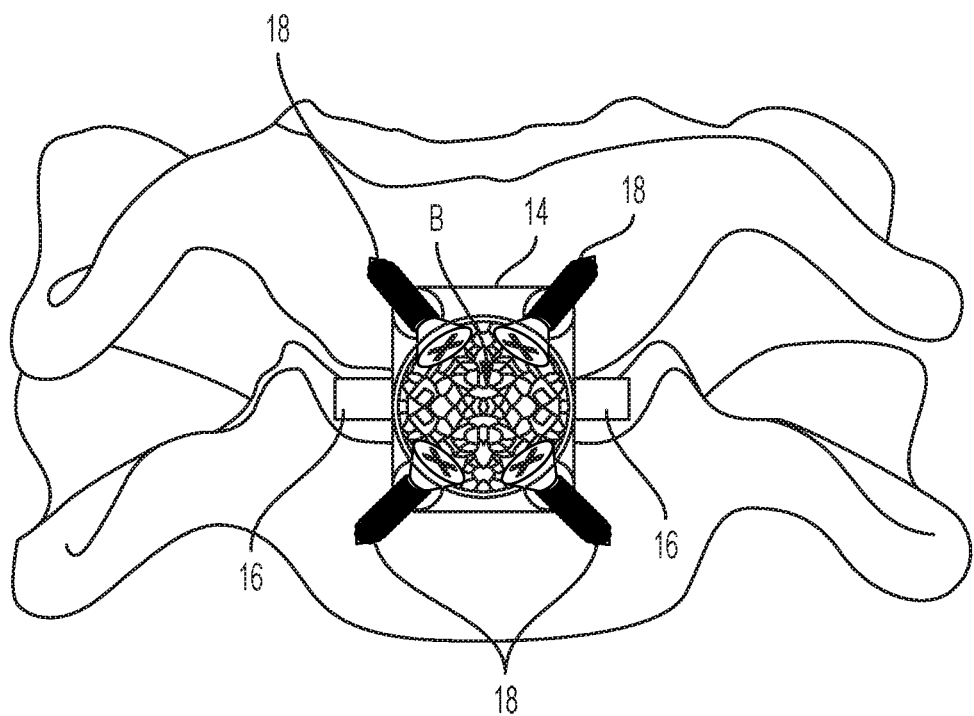
FIG. 5 is an illustration of the embodiment of the Cloward-style cervical mesh cage device of FIG. 3 inserted in the defect and having fasteners fastened to vertebral bodies and a bone graft material inserted into the cage device.
Figure 8:
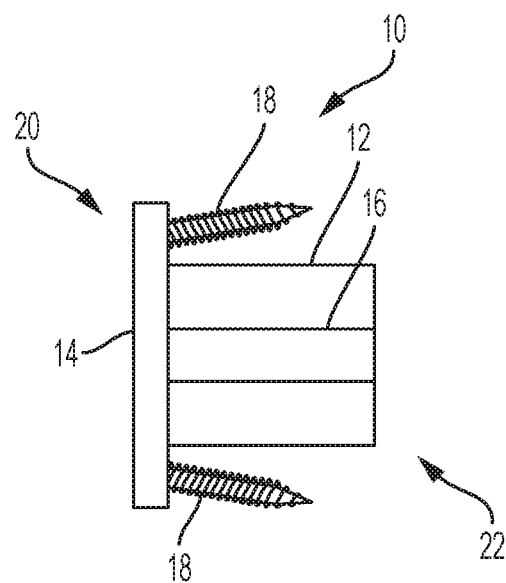
FIG. 8 is a side view of an embodiment of the Cloward-style cervical mesh cage device of FIG. 3 having fasteners.

FIGS. 4, 5, and 8, for example, illustrate the set of fastener apertures 24 in which one fastener 18 is located at each corner of the endplate 14. The set of fastener apertures 24 and endplate 14 may be configured such that fasteners 18 are flush with the endplate 14 when fastened. For example, the set of fastener apertures 24 may be countersunk within the endplate 14 or angled divergently with respect to the axis of the cylindrical body 12.

Figure 6:
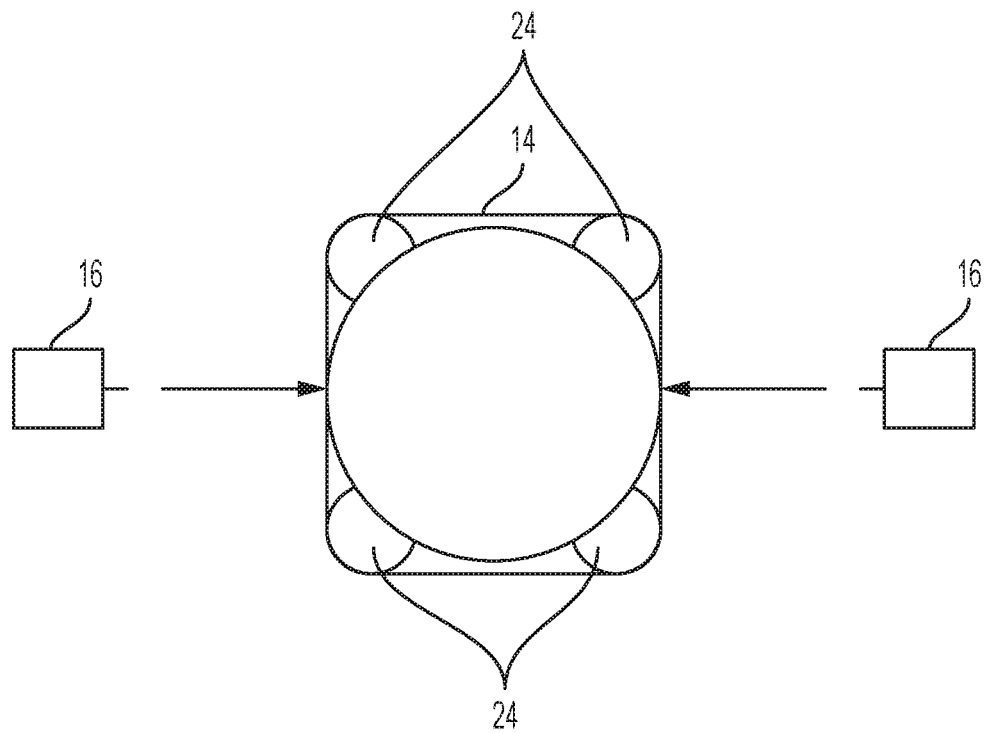
FIG. 6 is an illustration of an embodiment of the Cloward-style cervical mesh cage of FIG. 3 having lateral stabilizers unassembled from the cage device.
Figure 7:
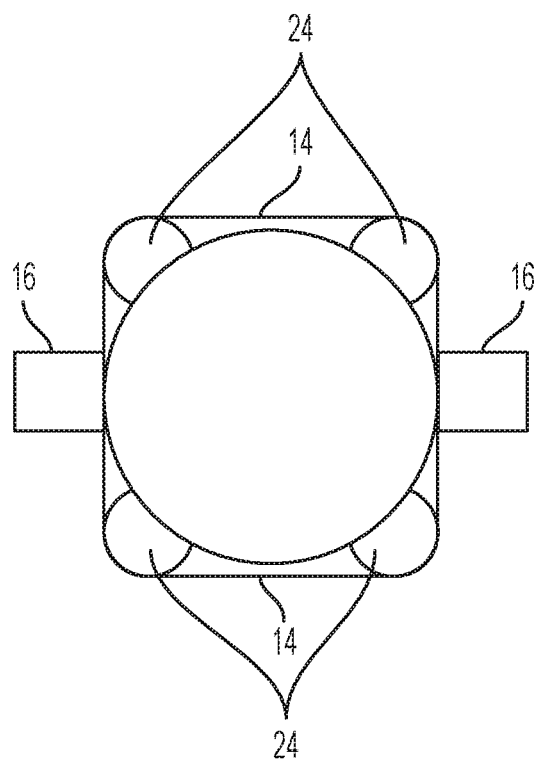
FIG. 7 is an illustration of an embodiment of the Cloward-style cervical mesh cage of FIG. 3 with lateral stabilizers assembled from the cage device.

In the current embodiment, the lateral stabilizers 16 are a pair of removable wings 16 (see FIGS. 6 and 7). The wings 16 are removable and customizable, such that the physician can customize the size of the wings 16 in accordance with various aspects of the patient, such as the opening/aperture diameter, cervical width, amount of residual compression, interbody opening height, etc. Various height and depth choices are available to accommodate a patient's individual anatomy. Furthermore, the lateral stabilizers 16 are configured to prevent the device 10 from rotating within the defect D and from laterally shifting within the defect D. For example, at least a portion of the lateral stabilizers 16 of the current embodiment fit between the interbody bones to prevent rotation of the device 10. In some embodiments, at least a portion of the lateral stabilizers 16 are in the defect D, and in yet another embodiment, at least a portion of the lateral stabilizers 16 are in the defect D and are adjacent to bone graft material B to promote bone growth. For example, the lateral stabilizers 16 may be configured to promote bone growth by having an outer surface treatment, such as roughened or porous surface, or the like, or a plurality of apertures, such as described above for the outer surface of the cylindrical body 12.

The lateral stabilizers 16, such as the pair of removable wings 16, may be configured to be slidably attached to the cylindrical body 12. For example, the removable wings 16 may include a dovetail-like joint, such that the removable wings 16 slide axially along a pair of grooves on the outer surface of the cylindrical body 12.

The grooves may be configured to prevent the removable wings 16 from moving radially when placed in the grooves. In one embodiment, the device 10 is configured to limit the pair of removable wings 16 from sliding from the proximal end 20 or distal end 22 of the cylindrical body 12. For example, inner ends of the removable wings 16 that fit within the grooves may be configured to frictionally fit within the groove, such that the inner ends having a ramp-like portion that angles from anterior to posterior ends of the removable wings (e.g., from the proximal end 20 to distal end 22 of the cylindrical body 12). The ramp-like portion increases the friction between the removable wings 16 and the grooves, thus substantially securing the removable wings 16 to the cylindrical body 12. Alternatively, the grooves may have a ramp-like portion that angles from proximal end 20 to distal end 22 of the cylindrical body 12, and the ramp-like portion increases the friction between the removable wings 16 and the groove, thus substantially securing the removable wings 16 to the cylindrical body 12. As a further alternative, the removable wings 16 may include locking mechanisms, such as fasteners, to secure the removable wings 16 to the cylindrical body 12.

The device 10 may be formed of many materials, such as metals, plastics, ceramics, or the like, that are biocompatible and/or approved for medical use. In the current embodiment, the device 10 is at least partially formed of materials that promotes bone growth and fusion to the device 10. For example, the device 10 may be formed of a stainless steel alloy, a titanium alloy, polyether ether ketone (PEEK), polyvinyl alcohol (PVA), or the like. Furthermore, the device 10 may be formed of multiple materials, for example, if the cylindrical body 12 is formed of a metal and the endplate 14 is formed of a plastic or a ceramic, or vice versa.

The device 10 may be manufactured according to common methods, such as additive manufacturing, extruding, injection molding, or the like. In addition, the device 10 can be manufactured by assembling multiple components that may each be manufactured according to common methods, such as those listed above. For example, the endplate 14 may be manufactured separately from a top portion and/or a bottom portion of the cylindrical body 12 and then assembled to form the cylindrical body 12 and the device 10. The lateral stabilizers 16 may be advantageously manufactured separately from other components to allow the physician to customize many dimensions of the device 10 according to the patient, as discussed above. Further, the surfaces of the lateral stabilizers 16 can be roughened surfaces, such as having teeth, grooves, and the like, to help prevent anterior migration of device 10. The device 10 can also include an anterior metal extension that protrudes cephalad and caudal to prevent impaction of cage into the spinal canal.

A method for inserting and using the device 10 includes decompressing the midline of the patient's spine. Compression of the spine is typically caused by midline compression or foraminal disease. In the current embodiment, decompressing the spine includes drilling an aperture or defect D in the spine to remove a cylindrical portion of bone, such as by the anterior approach technique. The method includes assembling the device 10, such as assembling the device 10 according to the desired dimensions for the patient. For example, the device 10 may have particular sizes of the cylindrical body 12, the endplate 14, and the lateral stabilizers 16. The method further includes inserting the device 10 into the defect D. In one embodiment, inserting the device 10 includes operating a tool to insert the device 10, and another embodiment includes inserting the device 10 into the defect D using hand force. The method also includes securing the device 10 to the interbody discs. In one embodiment, securing the device 10 includes fastening fasteners 18 within the apertures 24 of the endplate 14. Thus, device 10 is inserted into the defect D.

Second Embodiment

Another embodiment of the Cloward-style mesh cage device 30 is shown in FIGS. 9-15. The cage device 30 includes a cylindrical body 32 formed of a top portion 34 and a bottom portion 36, and an endplate 38, and can further include a wedge insert 40. In the current embodiment, the wedge insert 40 can be included and, when included, is a pair of strut spacers, as further described below. Each of the top portion 34 and bottom portion 36 has a clamshell-like shape, such that the top portion 34 and the bottom portion 36 can be joined at a joint face 42 of each top portion 34 and bottom portion 36 to form a cylindrical-like shape, such as described above.

The endplate 38 is configured to be formed of a top endplate 44 and a bottom endplate 46, each of which are respectively fixed to the top portion 34 and bottom portion 36 of the cylindrical body 32. The endplate 38 is configured to be adjacent to an anterior face of the cervical bones when the cylindrical body 32 is in the defect D. The endplate 38 also allows the bone graft material B to be placed within the cylindrical body 32 when the device 30 is in the defect D. Thus, the endplate 38 forms a rectangular-like outer shape having a set of fastener apertures 48 in each corner, similar to the endplate 14 described above that has a generally rectangular-like outer shape with a central aperture and the set of fastener apertures 24.

Figure 12:
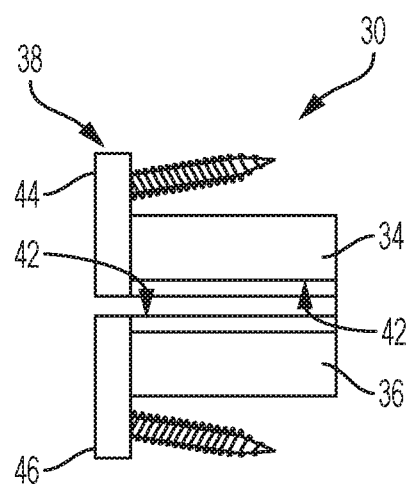
FIG. 12 is side view of the embodiment of the Cloward-style cervical mesh cage device of FIG. 9 having fasteners.
Figure 13:
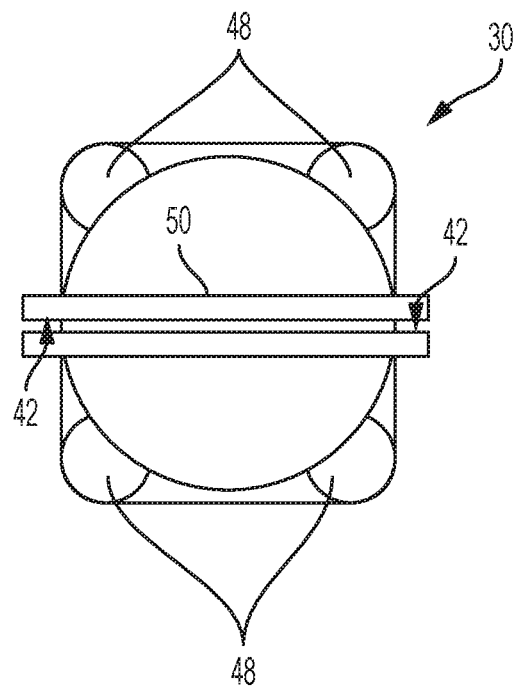
FIG. 13 is front view of the embodiment of the Cloward-style cervical mesh cage device of FIG. 9.
Figure 14:
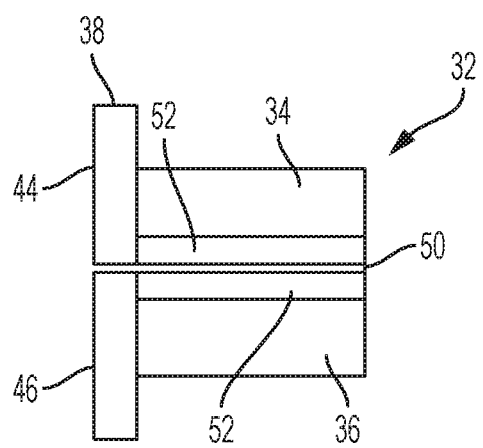
FIG. 14 is a side view of the embodiment of the Cloward-style cervical mesh cage device of FIG. 9 without fasteners at a lordotic angle of approximately 0 degrees.
Figure 15:
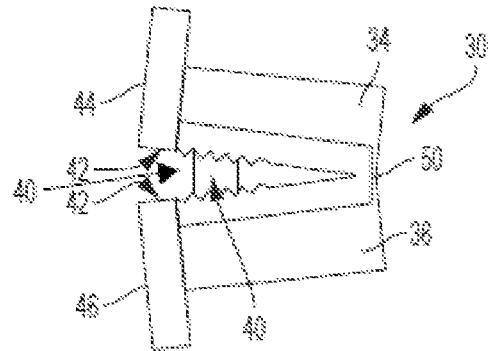
FIG. 15 is a side view of the embodiment of the Cloward-style cervical mesh cage device of FIG. 9 with strut spacers at a lordotic angle of approximately 12 degrees.

For example, FIGS. 12, 14, and 15 show each of the top portion 34 and the bottom portion 36 of the cylindrical body 32 having a semi-cylindrical-like shape, in which the top portion 34 and the bottom portion 36 have a cross-section that semi-circular-like. In the illustrated embodiment, the top portion 34 and the bottom portion 36 are joined by a joint 50 at the distal end of the cylindrical body 32. The joint 50 is configured to allow lordotic expansion, as required by the patient's needs. In other words, the cage device 30 has a slit that allows for lordotic expansion when needed. The joint 50 may be a hinge, bendable portion, or the like. Thus, the joint 50 allows the top portion 34 and the bottom portion 36 to form various angles, or lordotic angles, with respect to each other, and as further described below. The lordotic angle of the illustrated embodiment is approximately between 0 degrees and 12 degrees. For instance, FIG. 13 shows an embodiment that does not specifically include a wedge insert 40, and has a lordotic angle of 0 degrees. However, other embodiments have other lordotic angles, such as approximately 15 degrees, 20 degrees, and 25 degrees, etc.

Referring to FIG. 15, the joint faces 42 for each top portion 34 and bottom portion 36 of the illustrated embodiment is a face that is substantially flat between the proximal and distal ends of the device 30, and can mate to the opposite (e.g., top portion 34 or bottom portion 36) joint face 42 or mate to the pair of strut spacers (wedge insert 40), as further described below. For example, each of the joint faces 42 may include ridges, teeth, or the like that are configured to position the strut spacers on each of the joint faces 42.

Again referring to FIGS. 9-15, each of the top portion 34 and bottom portion 36 are configured to provide lateral support for the device 30 by fitting between the interbody discs. In the illustrated embodiment, each of the top portion 34 and the bottom portion 36 provides lateral support using lateral aspects or lateral stabilizers 52 that extend from the joint 50 of each top portion 34 and bottom portion 36 in a direction that is radially outward with respect to a central axis (e.g., extends radially away from and towards the central axis) of the cylindrical body 32 at the joint 50. Thus, the lateral stabilizers 52 can extend into the cylindrical body and the defect D. In another embodiment, the lateral stabilizers 52 extend from the joint 50 of each top portion 34 and bottom portion 36 in a direction that is radially away from the central axis.

Figure 9:
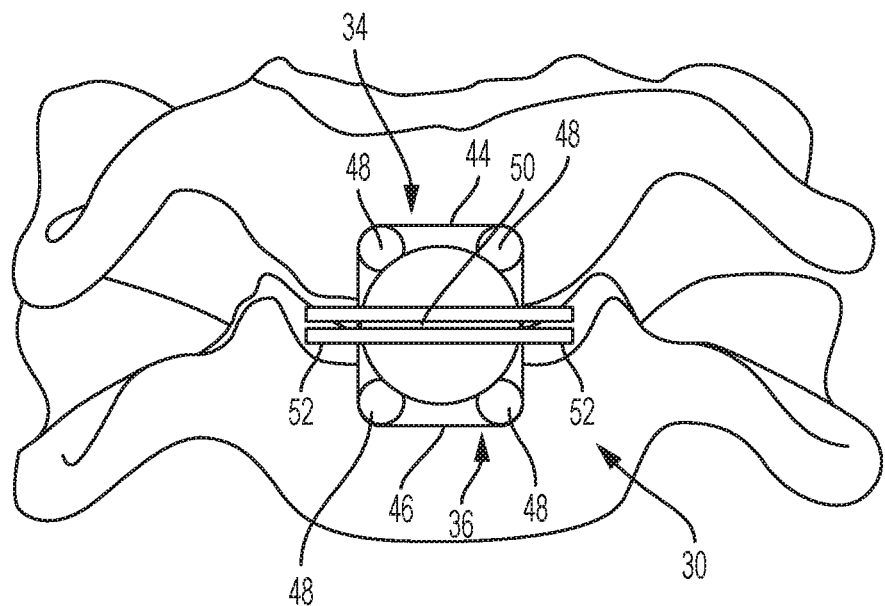
FIG. 9 is an illustration of an embodiment of the Cloward-style cervical mesh cage device for lordotic angles inserted in the drilled defect of FIG. 2.
Figure 10:
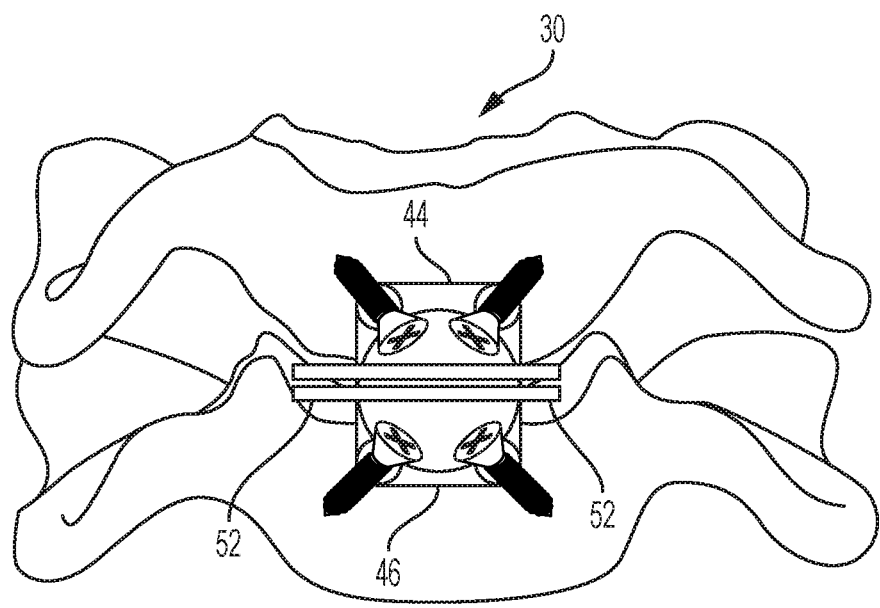
FIG. 10 is an illustration of the embodiment of the Cloward-style cervical mesh cage device of FIG. 9 inserted in the defect and having fasteners fastened to vertebral bodies.
Figure 11:
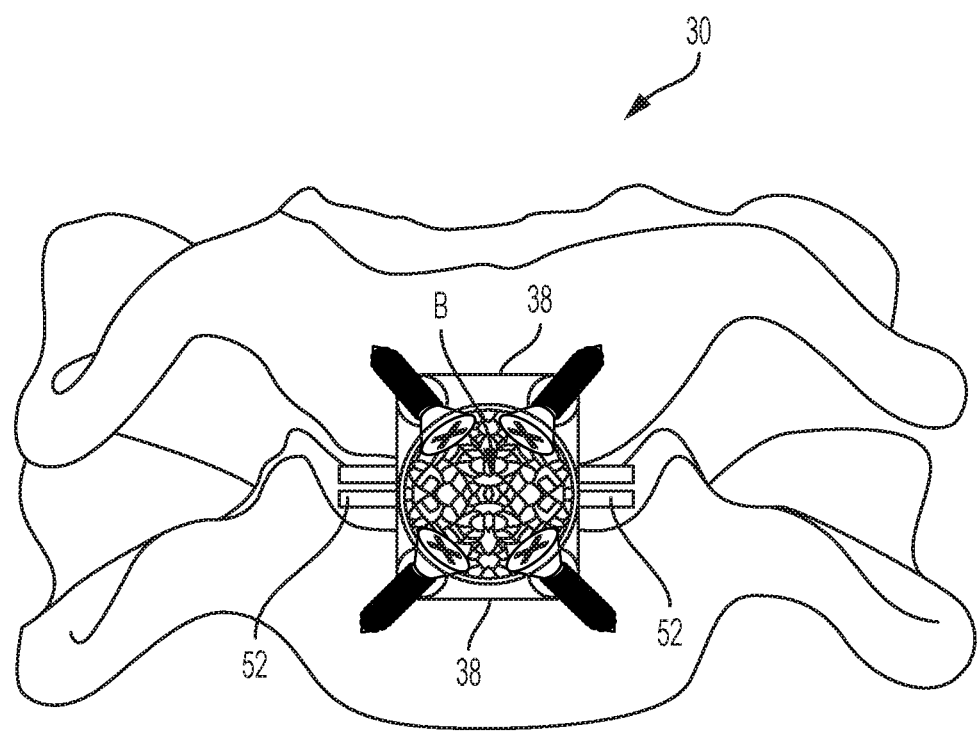
FIG. 11 is an illustration of the embodiment of the Cloward-style cervical mesh cage device of FIG. 9 inserted in the defect and having fasteners fastened to vertebral bodies and a bone graft material inserted into the cage device.

The lateral stabilizers 52 are configured to prevent the device 30 from rotating within the defect D and from laterally shifting within the defect D (see FIGS. 9-11). For example, at least a portion of the lateral stabilizers 16 of the current embodiment fit between the interbody bones to prevent rotation of the device 10. In another embodiment, the lateral stabilizers 52 are removable and can be various sizes, such as described above, to allow a physician to assemble the device 30 having the required size device 30 for the patient's requirements.

The strut spacers 40 (see FIG. 15) are configured to fix the lordotic expansion of the device 30 for the patient. The strut spacers 40 have teeth, ridges, or the like that mate to each of the joint faces 42 of the cylindrical body 32, such as to the lateral aspects of the lateral stabilizers 52. The strut spacers 40 may mate to each of the joint faces 42 at various positions between the distal end and the proximal end of the cylindrical body 32. Thus, the strut spacers 40 secure the lordotic angle between the top portion 34 and the bottom portion 36 of the cylindrical body 32 depending on where the strut spacers 40 are fixed along each of the joint faces 42 (e.g., using a trigonometric function). For example, the lordotic angle may be smaller if the strut spacers 40 are fixed near the proximal end of the cylindrical body 32, as compared to if the strut spacers 40 are fixed near the distal end of the cylindrical body 32. Further, the surfaces of the lateral stabilizers 52 can be roughened surfaces, such as having teeth, grooves, and the like, to help prevent anterior migration of device 30. The device 30 can also include an anterior metal extension that protrudes cephalad and caudal to prevent impaction of cage into the spinal canal.

A method for inserting the cage device 30, as described above, is similar to the method described above, and includes decompressing the midline of the patient's spine. In the illustrated embodiment shown in FIGS. 1, 2, and 9-11, decompressing the spine includes drilling an aperture or defect D in the spine to remove a cylindrical portion of bone, such as by the anterior approach technique. The method includes inserting the device 30 into the defect D. In one embodiment, inserting a cylindrical body 32 and lateral stabilizers 52 includes operating a tool to insert the device 30, and another embodiment includes inserting the device 30 into the defect D using hand force. The method also includes adjusting a lordotic angle of the device 30, and securing the lordotic angle of the device 30. The method further includes positioning a pair of strut spacers 40 in the cylindrical body 32 and lateral stabilizers 52 of the device 30. The method also includes securing the device 30 to the interbody discs. In one embodiment, securing the device 30 includes fastening fasteners within apertures 48 of the endplate 38. Thus, device 30 is inserted into the defect D.

The materials and methods of manufacture discussed above can also be applied to the present embodiment.

Third Embodiment

Figure 16:
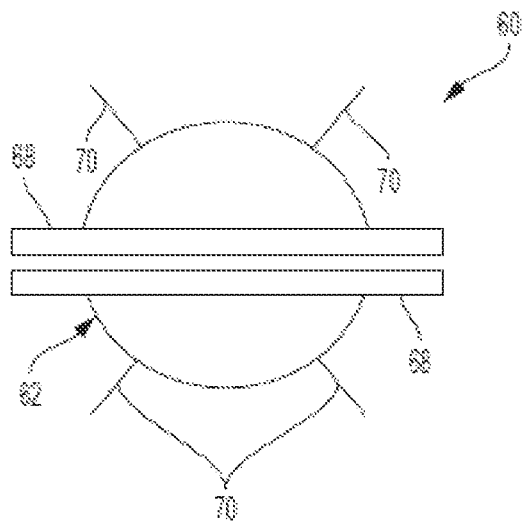
FIG. 16 is front view of the Cloward-style cervical mesh cage device according to another embodiment without an endplate.
Figure 17:
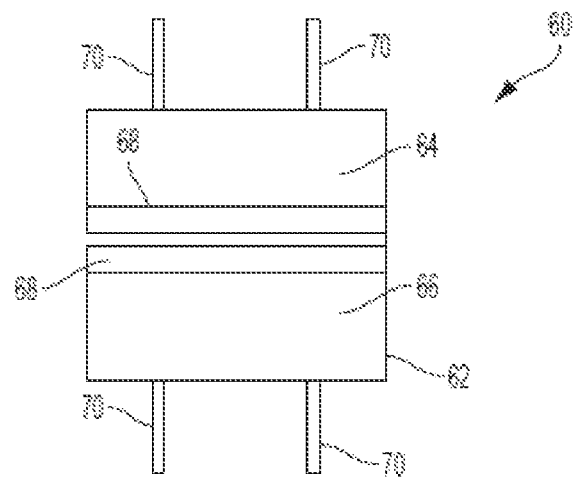
FIG. 17 is a side view of the embodiment of the Cloward-style cervical mesh cage device of FIG. 16 without an endplate and having fasteners configured to be secured from within the cage device.
Figure 18:
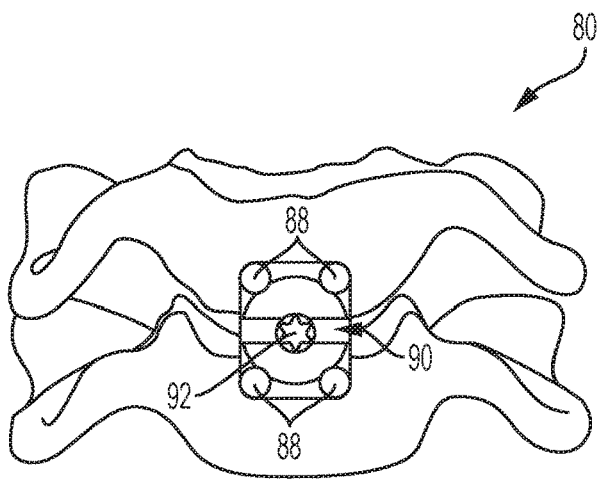
FIG. 18 an illustration of an embodiment of the Cloward-style cervical mesh cage device having an expandable lateral stabilization mechanism inserted in the drilled defect of FIG. 2.

Still another embodiment of the Cloward-style mesh cage device 60 is shown in FIGS. 16 and 17. The cage device 60 is similar to the cage device 30 of FIGS. 9-15, as described above, including a cylindrical body 62 formed of a top portion 64 and a bottom portion 66, and can include a pair of strut spacers. However, the cage device 60 is configured to fit entirely within the defect D. Thus, the cage device 60 lacks an endplate that is configured to be adjacent to an anterior face of the cervical bones. Each of the top portion 64 and bottom portion 66 has a clamshell-like shape, such that the top portion 64 and the bottom portion 66 can be joined at a joint face 68 of each top portion 64 and bottom portion 66 to form a cylindrical-like shape, such as described above. Thus, the top portion 64 and bottom portion 66 form lateral stabilizers having joint faces, as described above. The lateral stabilizers can be removable or fixed to the cylindrical body 62. Furthermore, the cylindrical body 62 is configured to be fixed within the defect D using fasteners. As such, the cylindrical body 62 can include integrated fixation holes that allow the cage device 60 to be secured to a vertebral body from within the cage device 60. In the illustrated embodiment of FIGS. 16 and 17, the fasteners are pins 70, although other fasteners may be used, such as screws, bone anchors, or the like. Further, the surfaces of the lateral stabilizers of the present embodiment can be roughened surfaces, such as having teeth, grooves, and the like, to help prevent anterior migration of device 60. The device 60 can also include an anterior metal extension that protrudes cephalad and caudal to prevent impaction of cage into the spinal canal.

A method for inserting the cage device 60, as described above, is similar to the methods described above, and includes decompressing the midline of the patient's spine. As such, decompressing the spine includes drilling an aperture or defect D in the spine to remove a cylindrical portion of bone, such as by the anterior approach technique. The method includes inserting the device 60 into the defect D. In one embodiment, inserting a cylindrical body 62 includes operating a tool to insert the device 30, and another embodiment includes inserting the device 60 into the defect D using hand force. The method also includes adjusting a lordotic angle of the device 60, and securing the lordotic angle of the device 60. The method further includes positioning a pair of strut spacers in the cylindrical body 62 of the device 60. The method also includes securing the device 60 to the interbody discs. In an embodiment of the method, the top portion 64 and bottom portion 66 can be secured to the interbody discs via the one or more fixation holes.

The materials and methods of manufacture discussed above can also be applied to the present embodiment.

Fourth Embodiment

Figure 22:
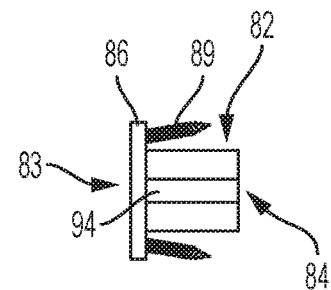
FIG. 22 is a side view of the embodiment of the Cloward-style cervical mesh cage device of FIG. 18 having fasteners.

In a further embodiment, the Cloward-style mesh cage device 80 is shown in FIGS. 18-22. As seen in FIG. 22, the Cloward-style mesh cage device 80 includes a cylindrical body 82 having a proximal end 83 and a distal end 84. The cylindrical body 82 can also be configured to promote bone growth by providing a plurality of apertures in the cylindrical body 82, such as a mesh, or an outer surface treatment to the cylindrical body 82. The Cloward-style mesh cage device 80 also has an endplate 86 that is fixed to the cylindrical body 82 at a proximal end 83, and the endplate can contain fastener apertures 88. The fastener apertures 88 are similar to the fastener apertures discussed in detail above, and can, for example, angled divergently from an axis running through the cylindrical body. Further, as seen in FIG. 22, fasteners 89, such as screws, bone anchors, or the like, can be used to fix the case device 80 to vertebral bodies via the fastener apertures 88, as discussed and explained above.

In the present embodiment, the cage device 80 contains an expandable lateral stabilization mechanism 90. The expandable lateral stabilization mechanism 90 includes a cage expansion mechanism 92 and a lateral stabilizer 94. The lateral stabilizer 94 can be a pair of wings that are contained within the cylindrical body 82 such that cage device 80 can be inserted into a defect D, discussed in detail above, while the lateral stabilizer 94 is contained within the cylindrical body 82. To allow the lateral stabilizer 94 to be contained in the cylindrical body 82, the lateral stabilizer 94 can be angled internally. For instance, when the cylindrical body 82 is a pair of wings, each of the wings of the pair of wings can be angled such that both wings fit within the cylindrical body 82.

Figure 19:
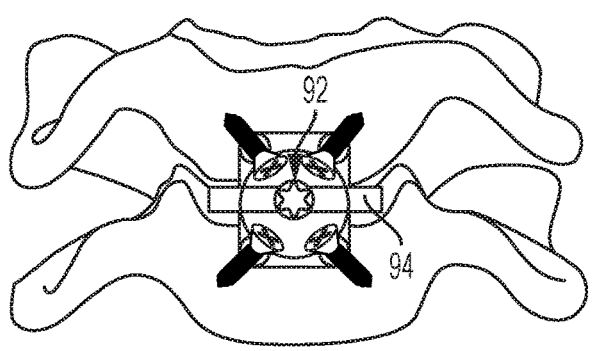
FIG. 19 is an illustration of the embodiment of the Cloward-style cervical mesh cage device of FIG. 18 inserted in the defect and having fasteners fastened to vertebral bodies.
Figure 20:
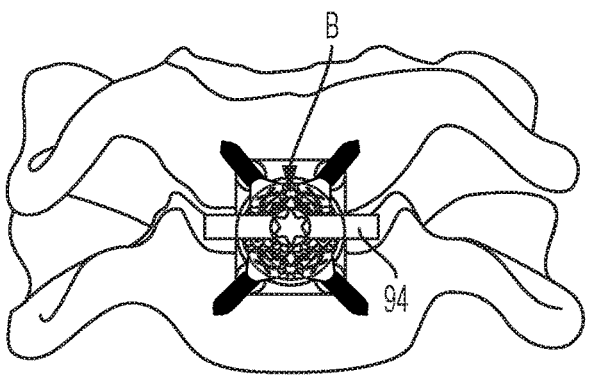
FIG. 20 is an illustration of the embodiment of the Cloward-style cervical mesh cage device of FIG. 18 inserted in the defect and having fasteners fastened to vertebral bodies and a bone graft material inserted into the cage device.
Figure 21:
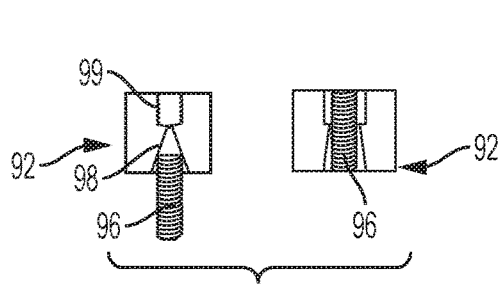
FIG. 21 is an illustration of an embodiment of a cage expansion mechanism the Cloward-style cervical mesh cage device of FIG. 18 where an expansion screw is being inserted into the cage expansion mechanism.

The cage expansion mechanism 92 can cause the expandable lateral stabilization mechanism to expand in a radial direction from the cylindrical body 82, as seen in FIG. 19. In an embodiment, the cage expansion mechanism 92 includes an expansion screw 96 and angled inner walls 98. The angled inner walls 98 can be part of or fixed to the lateral stabilizer 94. As the expansion screw 96 is inserted or screwed into the cage expansion mechanism 92, outward force from the expansion of the cage expansion mechanism 92 causes the lateral stabilizer 94 to expand out of the cylindrical body 82 in a radial direction. Further, the cage expansion mechanism 92 can include a receiving portion 99 configured to receive the expansion screw 96 by, for example, having threads configured to mate with the threads of the expansion screw 96. The cage expansion mechanism 92 can be fixed to the distal end 84 of the cylindrical body 82 and/or the inner surface of the cylindrical body 82. When the expansion screw 96 is fully inserted into the case expansion mechanism 92 (i.e., the expansion screw 96 is fully tightened), the lateral stabilizer 94 is fully deployed such that the lateral stabilizer 94 extends from the cylindrical body 82 in a radial direction, and also can lock the cage expansion mechanism 92 in place. Further, the surfaces of the lateral stabilizer 94 can be roughened surfaces, such as having teeth, grooves, and the like, to help prevent anterior migration of device 80. The device 80 can also include an anterior metal extension that protrudes cephalad and caudal to prevent impaction of cage into the spinal canal.

A method for inserting the cage device 80, as described above, is similar to the methods described above, and includes decompressing the midline of the patient's spine. Decompressing the spine includes drilling an aperture or defect D in the spine to remove a cylindrical portion of bone, such as by the anterior approach technique. The method includes inserting the device 60 into the defect D. In one embodiment, inserting a cylindrical body 82 includes operating a tool to insert the device 80, and another embodiment includes inserting the device 80 into the defect D using hand force. The method also includes the expansion of the cage expansion mechanism 92 to deploy the lateral stabilizer 94 from the cylindrical body 82, and can be done via hand force or using a tool, such as a manual, pneumatic, or electric screwdriver, hex key, and the like. The method also includes securing the device 80 to the interbody discs with the fasteners 89, as discussed above. The device 80 can be secured before, during, or after the expansion of the cage expansion mechanism 92 to deploy the lateral stabilizer 94 from the cylindrical body 82. Bone graft material B can be placed in the cylindrical body 82. As discussed above, a bone graft, such as the bone graft material B, can assist with the fixation of the cage device 80 to the interbody discs from within the defect D. The cylindrical body 82, therefore, can include a plurality of apertures, such as those of a mesh, and can also include an outer surface treatment to promote bone growth.

The materials and methods of manufacture discussed above can also be applied to the present embodiment.

The invention claimed is:

1. A cervical mesh cage device comprising:
a cylindrical body comprising a top portion and a bottom portion, wherein the cylindrical body has a proximal end and a distal end,
an endplate comprising a top endplate and a bottom endplate,
wherein the top endplate is fixed to the top portion of the cylindrical body at the proximal end,
wherein the bottom endplate is fixed to the bottom portion of the cylindrical body at the proximal end, and
wherein the endplate comprises fastener apertures, and
a lateral stabilizer,
wherein the top portion of the cylindrical body and the bottom portion of the cylindrical body are joined by a joint at the distal end of the cylindrical body, and
wherein the lateral stabilizer extends from the top portion of the cylindrical body and the bottom portion of the cylindrical body in a direction that is radially outward with respect to a central axis of the cylindrical body.

2. The cervical mesh cage device according to claim 1, further comprising a wedge insert.

3. The cervical mesh cage device according to claim 1, wherein the top portion of the cylindrical body and the bottom portion of the cylindrical body have joint faces that are configured to mate the top portion of the cylindrical body with the bottom portion of the cylindrical body.

4. The cervical mesh cage device according to claim 2, wherein the wedge insert is a pair of strut spacers, and wherein the top portion of the cylindrical body and the bottom portion of the cylindrical body have joint faces that are configured to mate the top portion of the cylindrical body with a top portion of the strut spacers and the bottom portion of the cylindrical body with a bottom portion of the strut spacers.

5. The cervical mesh cage device according to claim 1, further comprising a plurality of fasteners configured to fix the cervical mesh cage device to both a first cervical vertebra and a second cervical vertebra via the fastener apertures.

6. The cervical mesh cage device according to claim 5, wherein the top portion of the cylindrical body and the bottom portion of the cylindrical body are joined by the joint such that an angle between the top portion of the cylindrical body and the bottom portion of the cylindrical body is between 0 degrees and approximately 25 degrees.

7. The cervical mesh cage device according to claim 1, wherein the lateral stabilizer further extends into the cylindrical body.

8. The cervical mesh cage device according to claim 4, wherein the strut spacers are configured to fix an angle between the top portion of the cylindrical body and the bottom portion of the cylindrical body.

9. A method of inserting the cervical mesh cage device according to claim 1 comprising:
- drilling a defect in a spine to remove a portion of bone;
- inserting the cervical mesh cage device into the defect; and
- fastening the cervical mesh cage device to a first cervical vertebra and a second cervical vertebra in the spine.

10. The method according to claim 9, further comprising placing a bone graft material into the cylindrical body.

* * * * *